United States Patent
Isch

(10) Patent No.: US 9,566,162 B2
(45) Date of Patent: Feb. 14, 2017

(54) ADJUSTABLE HUMERAL TRAY FOR SHOULDER ARTHROPLASTY

(71) Applicant: Biomet Manufacturing, LLC, Warsaw, IN (US)

(72) Inventor: Bryce Isch, Warsaw, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 0 days.

(21) Appl. No.: 14/636,770

(22) Filed: Mar. 3, 2015

(65) Prior Publication Data

US 2016/0256287 A1 Sep. 8, 2016

(51) Int. Cl.
*A61F 2/40* (2006.01)
*A61F 2/46* (2006.01)
*A61F 2/30* (2006.01)

(52) U.S. Cl.
CPC .......... *A61F 2/4003* (2013.01); *A61F 2/4014* (2013.01); *A61F 2/4612* (2013.01); *A61F 2002/30331* (2013.01); *A61F 2002/30332* (2013.01); *A61F 2002/30398* (2013.01); *A61F 2002/30594* (2013.01); *A61F 2002/30604* (2013.01); *A61F 2002/4022* (2013.01)

(58) Field of Classification Search
CPC ........ A61F 2/4003; A61F 2/46; A61F 2/4612; A61F 2002/30331; A61F 2/40; A61F 2/4081; A61F 2/4059; A61F 2002/4096; A61F 2002/4092; A61F 2002/4085; A61F 2002/4088
USPC ............................................ 623/19.11–19.14
See application file for complete search history.

(56) References Cited

U.S. PATENT DOCUMENTS

| 5,336,268 | A | * | 8/1994 | Rispeter | A61F 2/3609 623/22.4 |
| 5,645,607 | A | * | 7/1997 | Hickey | A61B 17/1659 623/23.35 |
| 5,702,447 | A | * | 12/1997 | Walch | A61F 2/4081 606/309 |
| 6,197,062 | B1 | * | 3/2001 | Fenlin | A61F 2/4014 623/19.12 |
| 6,530,957 | B1 | * | 3/2003 | Jack | A61F 2/4684 623/19.14 |
| 6,749,637 | B1 | * | 6/2004 | Bahler | A61F 2/4014 623/19.11 |

(Continued)

FOREIGN PATENT DOCUMENTS

WO  WO-2014138061 A1  9/2014

OTHER PUBLICATIONS

"International Application Serial No. PCT/US2016/020387, International Search Report mailed May 6, 2016", 7 pgs.

(Continued)

*Primary Examiner* — Alvin Stewart
(74) *Attorney, Agent, or Firm* — Schwegman Lundberg & Woessner, P.A.

(57) ABSTRACT

An adjustable humeral implant includes a humeral tray and a humeral coupler. The humeral tray includes a humeral coupler receiving portion. The humeral coupler includes a humeral tray mating portion and a stem portion extending from the humeral tray mating portion along a first axis. The humeral tray mating portion is translatable within the humeral coupler receiving portion in a direction transverse to the first axis.

16 Claims, 7 Drawing Sheets

(56) References Cited

U.S. PATENT DOCUMENTS

| | | | | |
|---|---|---|---|---|
| 8,647,387 B2* | 2/2014 | Winslow | A61F 2/4014 128/898 |
| 8,663,333 B2* | 3/2014 | Metcalfe | A61F 2/4014 623/19.11 |
| 8,920,509 B2* | 12/2014 | Katrana | A61F 2/3804 623/21.12 |
| 2001/0053935 A1* | 12/2001 | Hartdegen | A61F 2/4684 623/19.12 |
| 2002/0095214 A1* | 7/2002 | Hyde, Jr. | A61B 17/1604 623/18.12 |
| 2002/0120339 A1 | 8/2002 | Callaway et al. | |
| 2002/0156534 A1* | 10/2002 | Grusin | A61F 2/4014 623/19.14 |
| 2004/0064188 A1* | 4/2004 | Ball | A61F 2/4014 623/19.11 |
| 2004/0064190 A1* | 4/2004 | Ball | A61F 2/4014 623/19.14 |
| 2005/0033443 A1* | 2/2005 | Blatter | A61F 2/4014 623/19.14 |
| 2005/0288791 A1* | 12/2005 | Tornier | A61F 2/32 623/19.13 |
| 2007/0050040 A1* | 3/2007 | Guederian | A61F 2/4014 623/19.14 |
| 2007/0112430 A1* | 5/2007 | Simmen | A61F 2/40 623/19.14 |
| 2007/0198094 A1* | 8/2007 | Berelsman | A61F 2/4014 623/19.14 |
| 2007/0219637 A1* | 9/2007 | Berelsman | A61F 2/4081 623/19.11 |
| 2008/0234829 A1* | 9/2008 | Mutchler | A61F 2/4014 623/19.14 |
| 2009/0164021 A1* | 6/2009 | Dallmann | A61F 2/40 623/19.11 |
| 2009/0281630 A1* | 11/2009 | Delince | A61F 2/4081 623/19.13 |
| 2010/0076561 A1* | 3/2010 | Emmanuel | A61F 2/4014 623/19.11 |
| 2011/0118846 A1* | 5/2011 | Katrana | A61F 2/4014 623/19.13 |
| 2011/0295376 A1* | 12/2011 | Winslow | A61F 2/4014 623/19.14 |
| 2012/0130498 A1* | 5/2012 | Long | A61F 2/4081 623/19.11 |
| 2012/0179262 A1* | 7/2012 | Metcalfe | A61F 2/4014 623/19.14 |
| 2013/0066433 A1* | 3/2013 | Veronesi | A61F 2/4081 623/19.13 |
| 2013/0090736 A1* | 4/2013 | Katrana | A61F 2/4014 623/19.13 |
| 2013/0150973 A1* | 6/2013 | Splieth | A61F 2/4081 623/19.11 |
| 2013/0204375 A1 | 8/2013 | Winslow et al. | |
| 2013/0325134 A1* | 12/2013 | Viscardi | A61F 2/4014 623/19.14 |
| 2014/0025173 A1* | 1/2014 | Cardon | A61F 2/4081 623/19.13 |
| 2014/0156012 A1* | 6/2014 | Winslow | A61F 2/4014 623/19.14 |
| 2014/0188232 A1* | 7/2014 | Metcalfe | A61F 2/4014 623/19.14 |
| 2015/0134066 A1* | 5/2015 | Bachmaier | A61F 2/4014 623/19.14 |

OTHER PUBLICATIONS

"International Application Serial No. PCT/US2016/020387, Written Opinion mailed May 6, 2016", 7 pgs.

* cited by examiner

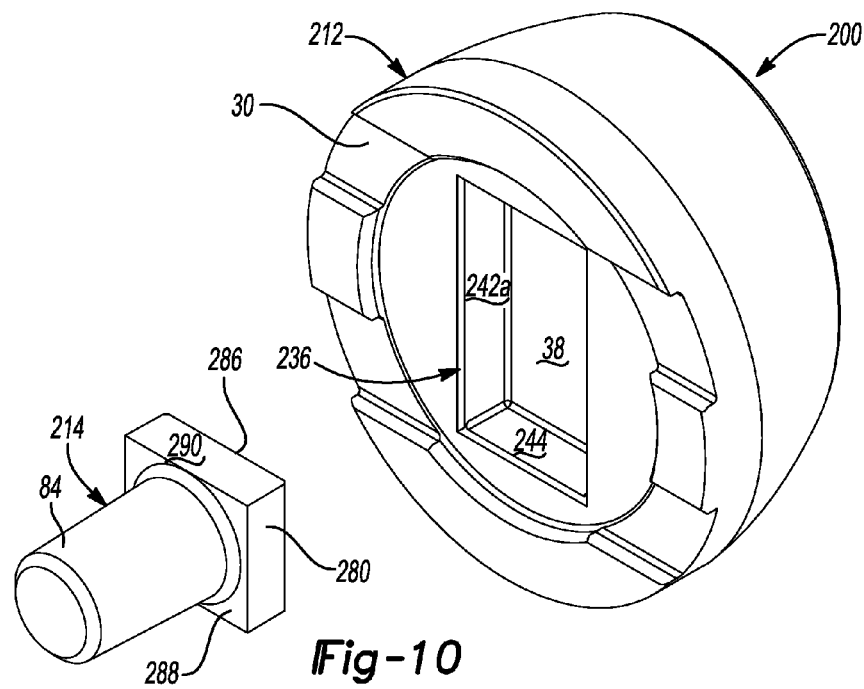
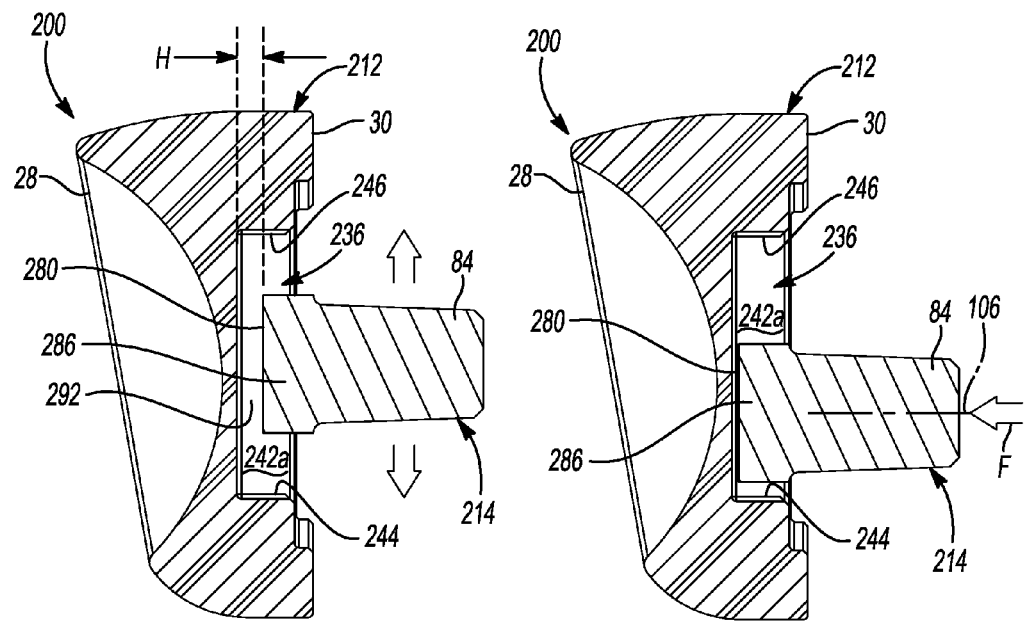
Fig-10
Fig-11A  Fig-11B

ADJUSTABLE HUMERAL TRAY FOR SHOULDER ARTHROPLASTY

FIELD

The present disclosure relates to an adjustable humeral implant for shoulder arthroplasty, and related methods of assembling and using an adjustable humeral implant.

BACKGROUND

This section provides background information related to the present disclosure and is not necessarily prior art.

Performing an anatomic or reverse arthroplasty generally requires the placement of a humeral implant (e.g., a glenosphere or a glenosphere-receiving implant such as a humeral tray) in, and/or relative to, a humerus. For example, it is often necessary to position the humeral implant relative to a surface of the resected humerus such that medial overhang of the humeral implant relative to the surface is minimized or eliminated. Considerable surgical skill is generally required to accurately align the humeral implant in the correct orientation in, and/or relative to, the humerus when performing the anatomic or reverse arthroplasty. It is desirable, therefore, that an adjustable humeral implant be accurately oriented relative to the humerus when performing an anatomic or reverse arthroplasty.

SUMMARY

This section provides a general summary of the disclosure, and is not a comprehensive disclosure of its full scope or all of its features.

According to one particular aspect, the present disclosure provides an adjustable humeral implant. The adjustable humeral implant may include a humeral tray and a humeral coupler. The humeral tray may include a humeral coupler receiving portion. The humeral coupler may include a humeral tray mating portion and a stem portion extending from the humeral tray mating portion along a first axis. The humeral tray mating portion may be configured to translatable within the humeral coupler receiving portion in a direction transverse to the first axis.

In some configurations, the humeral coupler receiving portion may include a channel. The humeral tray mating portion may be operable to translate within the channel.

In some configurations, the humeral tray mating portion may be configured to translate within the humeral coupler receiving portion in a direction substantially perpendicular to the first axis.

In some configurations, the adjustable humeral implant may include an adjustment member and a lock member. The adjustment member may be slidably received by an inferior edge of the humeral tray mating portion, and the lock member may be slidably received by a superior edge of the humeral tray mating portion.

In some configurations, the humeral tray may include first and second apertures in communication with the humeral coupler receiving portion. The adjustment member may be slidably received within the first aperture and the lock member may be slidably received within the second aperture.

In some configurations, the first and second apertures may include first and second openings, respectively, in an exterior peripheral surface of the humeral tray.

In some configurations, the humeral coupler may be rotatably received within the humeral coupler receiving portion.

In some configurations, the stem portion may extend from the humeral tray mating portion along a first axis. The humeral coupler may be configured to rotate within the humeral coupler receiving portion about the first axis and translate within the humeral coupler receiving portion in a direction substantially perpendicular to the first axis.

In some configurations, the humeral tray mating portion may be press-fit within the humeral coupler receiving portion.

In some configurations, the stem portion may include a male taper and the humeral coupler receiving portion may include a female taper. The male taper may be configured to frictionally engage the female taper.

According to another particular aspect, the present disclosure provides an adjustable humeral implant. The adjustable humeral implant may include a humeral coupler and a humeral tray. The humeral coupler may include a base and a stem extending from the base. The humeral tray may include a glenosphere-facing side and an opposed humerus-facing side, the humerus facing side may include a recess at least partially defined by a bottom surface and opposed flanges. The recess may be configured to slidably receive the base of the humeral coupler such that the opposed flanges secure the base within the recess.

According to yet another particular aspect, the present disclosure provides a method of assembling an adjustable humeral implant. The adjustable humeral implant may include a humeral tray and a humeral coupler configured to translate relative to the humeral tray. The method may include inserting a stem into a humerus having a cut surface. The method may also include securing the humeral coupler to the stem. The method may also include translating the humeral tray relative to the humeral coupler in a direction substantially parallel to the cut surface from a first position to a second position. The method may further include securing the humeral tray in the second position.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 10 is an exploded view of the adjustable humeral tray of FIG. 8;

FIG. 11A is a cross-sectional view of the adjustable humeral tray of FIG. 8 taken along the line 11A-11A and showing the adjustable humeral tray in a partially assembled configuration; and FIG. 11B is another cross-sectional view of the adjustable humeral tray similar to FIG. 11A and showing the adjustable humeral tray in a fully assembled configuration.

Corresponding reference numerals indicate corresponding parts throughout the several views of the drawings.

DETAILED DESCRIPTION

Example embodiments will now be described more fully with reference to the accompanying drawings.

Figure 3:
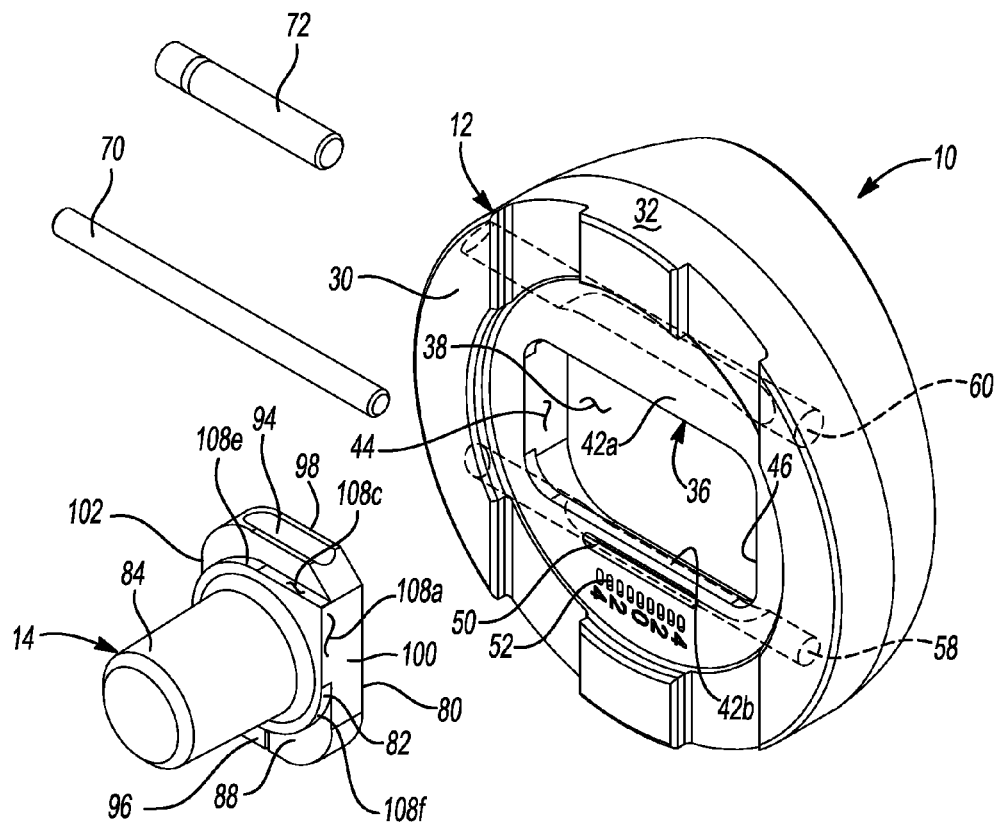
FIG. 3 is an exploded view of the adjustable humeral tray of FIG. 1.
Figure 4:
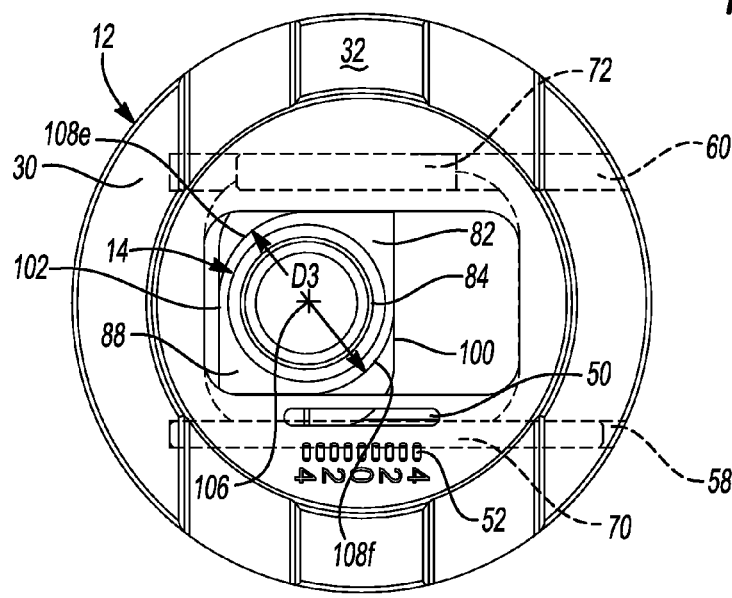
FIG. 4 is an end view of the of the first side of the adjustable humeral tray of FIG. 1.
Figure 5:
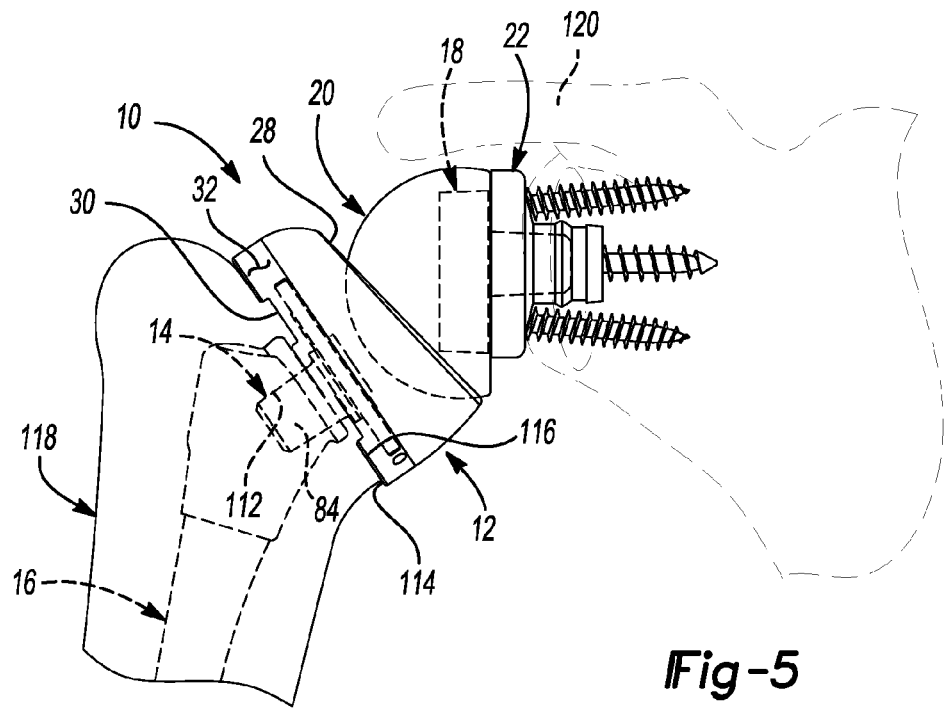
FIG. 5 is an environmental view of the adjustable humeral tray of FIG. 1.

Referring to FIGS. 1-7D, an adjustable implant 10 constructed in accordance with the present teachings is illustrated. The adjustable implant 10 may generally include a tray 12 and a coupler 14. According to one exemplary use, the adjustable implant 10 may be an adjustable humeral implant 10 configured for use in a shoulder joint replacement procedure. Specifically, as illustrated in FIG. 5, in some configurations, the adjustable humeral implant 10 may be configured for use in a reverse shoulder arthroplasty procedure. In this regard, as illustrated in FIG. 3, the adjustable implant 10 may further include a stem 16, a retainer 18, a glenosphere 20 and a baseplate 22. It will be appreciated, however, that the tray 12 and the coupler 14 may be adapted to fix various implants to various bones within the scope of the present teachings.

The tray 12 may include a first or glenosphere-receiving side 28, a second or coupler-receiving side 30 opposite the glenosphere-receiving side 28, and a peripheral surface 32 extending from the glenosphere-receiving side 28 to the coupler-receiving side 30. The glenosphere- and coupler-receiving sides 28, 30 may each define a substantially circular shape, such that the peripheral surface 32 includes a substantially cylindrical construct. The tray 12 can be formed from any biocompatible material, including a polymer, ceramic, metal, or combination thereof. In this regard, the tray 12 can be formed using any suitable manufacturing technique, including machining, injection or direct compression molding, and/or additive manufacturing techniques.

The glenosphere-receiving side 28 may include a recess 34. The coupler-receiving side 30 may include a channel or cavity 36. As will be explained in more detail below, the recess 34 may be configured to receive or otherwise mate with the glenosphere 20, and the cavity 36 may be configured to receive or otherwise mate with the coupler 14. In this regard, the cavity 36 may include, or otherwise be defined by, a bottom or first guide surface 38, a peripheral surface 40, and a flange or lip 42. As illustrated, the first guide surface 38 may be substantially planar. The peripheral surface 40 may surround or otherwise extend from the first guide surface 38. In this regard, the peripheral surface 40 may include first and second opposed ends or stop surfaces 44, 46. The stop surfaces 44, 46 may extend perpendicularly from the first guide surface 38. A distance D1 between the first and second stop surfaces 44, 46 may define a maximum travel path or adjustment distance for the coupler 14.

Figure 1:
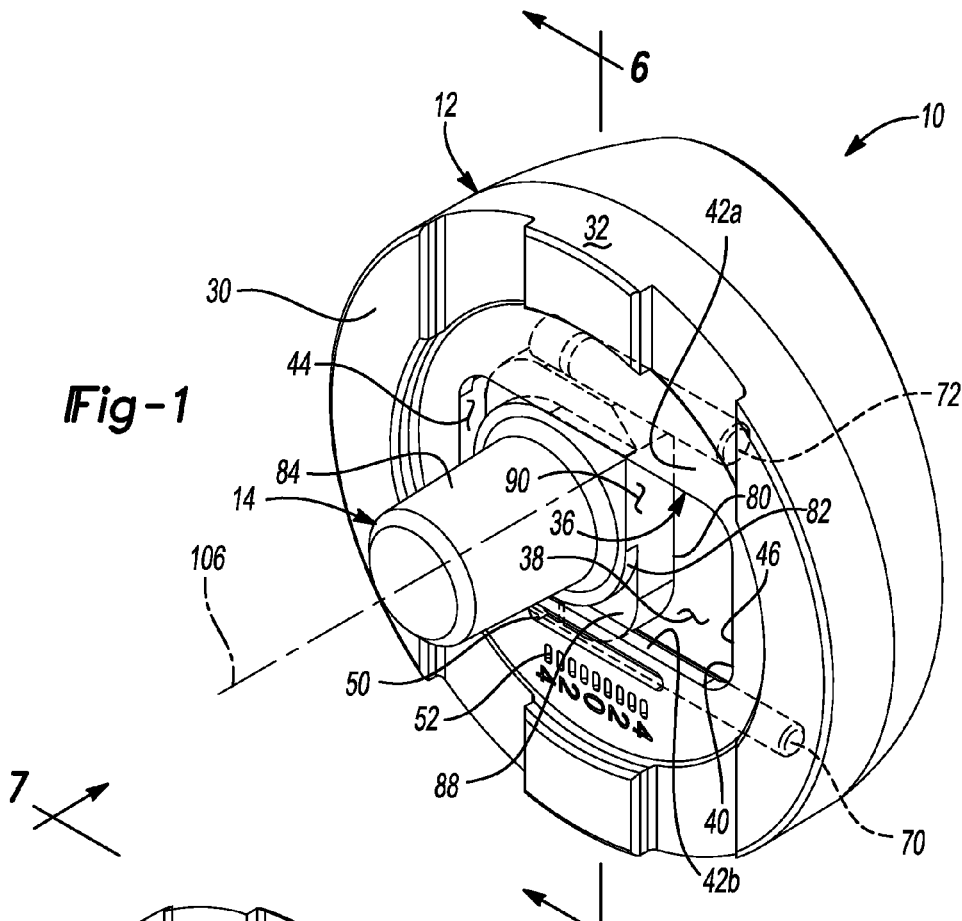
FIG. 1 is a perspective view of a first side of an adjustable humeral tray in accordance with the principles of the present disclosure.
Figure 2:
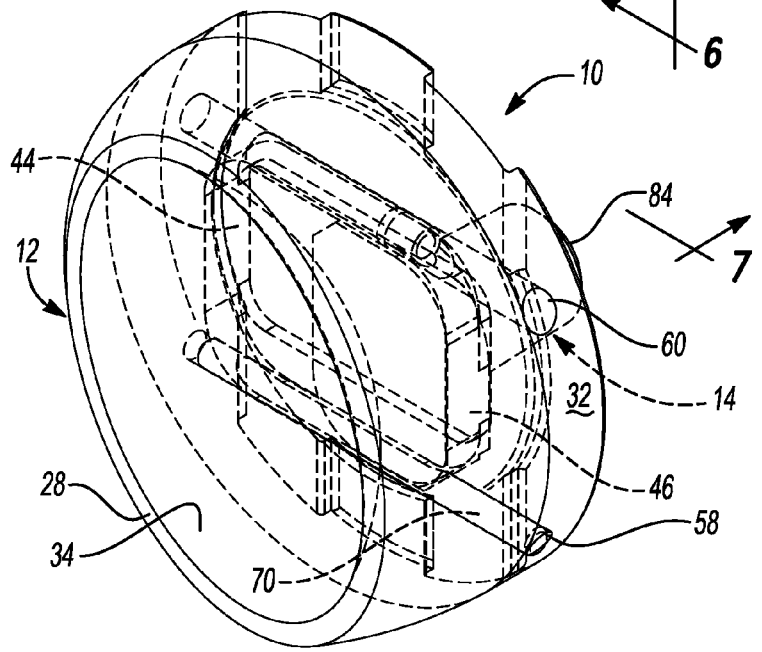
FIG. 2 is a perspective view of a second side of the adjustable humeral tray of FIG. 1.
Figure 7A:
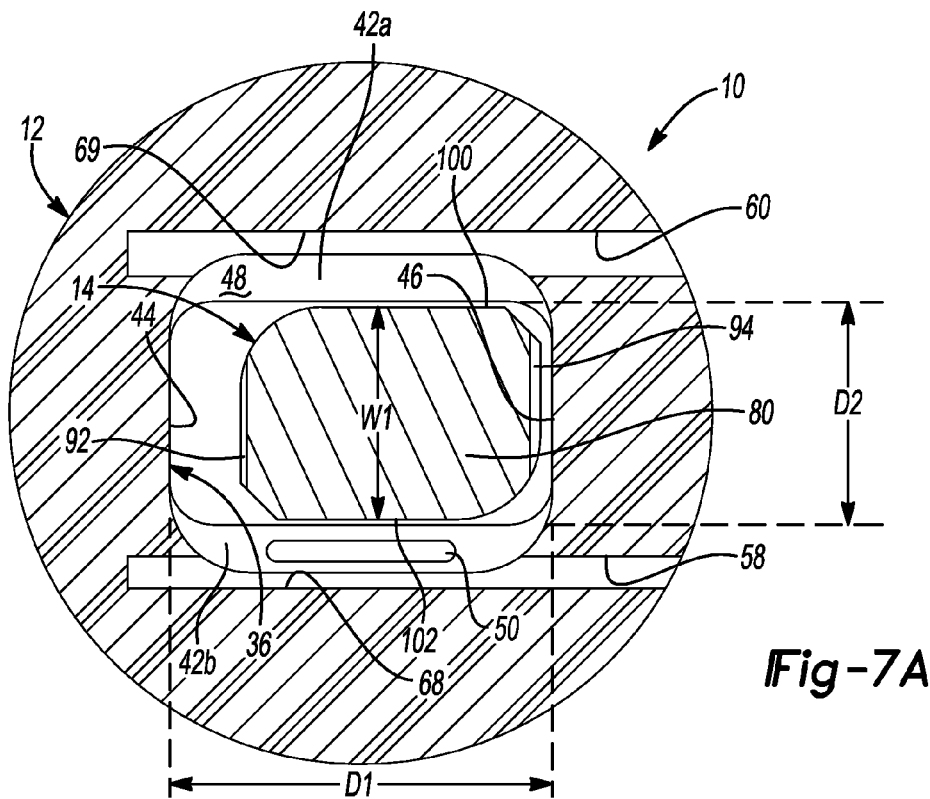
FIG. 7A is a cross-sectional view of the adjustable humeral tray of FIG. 1, taken along the line 7-7 of FIG. 2 and showing the adjustable humeral tray in a first partially assembled configuration.

The lip 42 may surround at least a portion of the peripheral surface 40. As illustrated, in some configurations the lip 42 may include opposed first and second portions 42a, 42b extending from and between the first and second stop surfaces 44, 46. The first and second portions 42a, 42b may define a distance D2 extending therebetween in a direction substantially perpendicular to the distance D1. The lip 42 may further include a second guide surface 48 generally facing the first guide surface 38. In this regard, in some configurations the second guide surface 48 may be substantially parallel to the first guide surface 38. At least one of the first and second portions 42a, 42b may include an aperture or window 50 in communication with the cavity 36. With particular reference to FIGS. 1 and 7A, the window 50 may include an oval or otherwise oblong shape. As will be explained in more detail below, the window 50 can allow a surgeon or other user of the implant 10 to view the location or position of the coupler 14 within the cavity 36. In this regard, at least one of the first and second portions 42a, 42b may also include a metering portion 52 having a series of divots, protrusions, or tick marks. The metering portion 52 can allow the surgeon to gage or otherwise measure the location or position of the coupler within the cavity 36. For example, the surgeon may use the tick marks of the metering portion to determine the distance between the coupler and the first and/or second stop surface 44, 46.

The peripheral surface 32 of the tray 12 may include first and second bores or apertures 58, 60. As illustrated in FIGS. 7A-7D, in some configurations the first and second apertures 58, 60 may extend through a portion of the tray 12. It will be appreciated, however, that the first and second apertures 58, 60 may extend completely through the peripheral surface 32 within the scope of the present disclosure.

The first aperture 58 may be located on a first side of the cavity 36 proximate the first portion 42a of the lip 42, and the second aperture 60 may be located on a second side of the cavity 36 (opposite the first side of the cavity 36) proximate the second portion 42b of the lip 42. In this regard, the first aperture 58 may extend in a direction substantially parallel to the second aperture 60. A portion of the first and second apertures 58, 60 may open into, or otherwise be in communication with, the cavity 36. Specifically, as illustrated in FIGS. 6 and 7A-7D, a central portion of each of the first and second apertures 58, 60 may open into the cavity 36, such that the central portion of each of the first and second apertures 58, 60 defines first and second grooves or channels 68, 69, respectively.

The implant 10 may further include an adjustment member or first pin 70, and a lock member or second pin 72. The first and second pins 70, 72 may be sized and shaped to be received within the first and second apertures 58, 60, respectively. In this regard, the first and second pins 70, 72 may have a substantially cylindrical shape, including an externally threaded portion configured to threadably engage an internally threaded portion of the first and/or second bores 58, 60, respectively. The second pin 72 may further include a slight taper extending from and between proximal and distal ends 74, 76, such that the proximal end 74 has a larger diameter or cross-sectional area than the distal end 76 (FIG. 7D). As will be explained in more detail below, the first and second pins 70, 72 can allow the surgeon to adjust or otherwise change the position of the coupler 14 relative to the tray 12 within the cavity 36, while the taper of the second pin 72 can help the surgeon to secure or otherwise lock the position of the coupler 14 relative to the tray 12 within the cavity 36.

Figure 6:
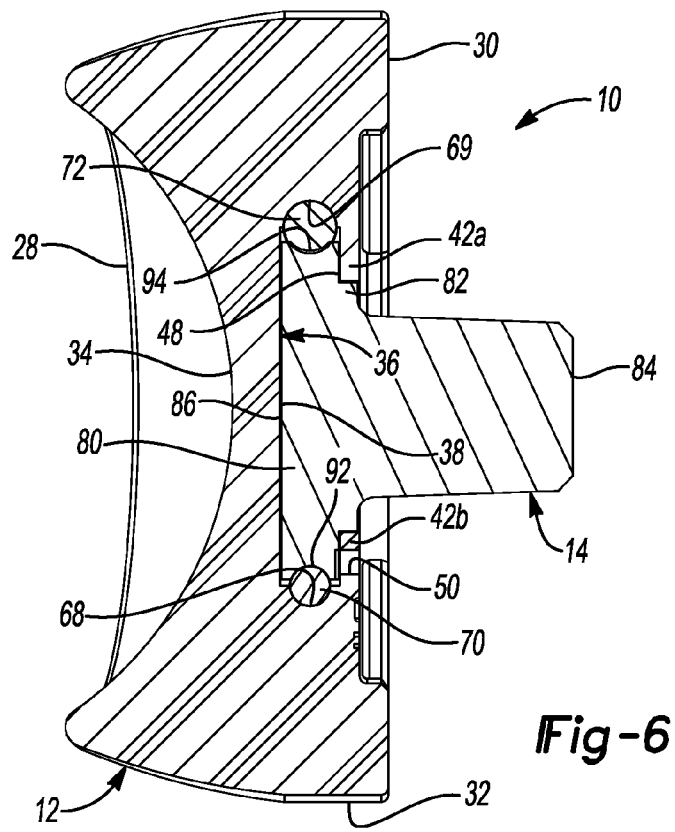
FIG. 6 is a cross-sectional view of the adjustable humeral tray of FIG. 1, taken along the line 6-6 of FIG. 1.

With reference to FIGS. 1, 3 and 6, the coupler 14 may include a tray-mating portion or base 80, a step 82, and a stem 84. In some configurations, the base 80, step 82, and stem 84 may be integrally formed such that the coupler 14 includes an integral or monolithic construct. It will be appreciated, however, that the base 80, step 82, and/or stem 84 may be separately formed and thereafter joined or assembled, within the scope of the present disclosure.

The base 80 may include a proximal side 86 (FIG. 6), a distal side 88 (FIG. 1), and a peripheral edge or surface 90 (FIG. 1) extending from and between the proximal and distal sides 86, 88. As will be explained in more detail below, in an assembled configuration, the proximal side 86 may face or otherwise slidably engage the first guide surface 38 and the distal side 88 may face or otherwise slidably engage the second guide surface 48. In this regard, in some configurations the proximal and/or distal sides 86, 88 may be substantially planar. The peripheral surface 90 may include first and second channels or grooves 92, 94 disposed on first and second opposing sides of the base 80. In this regard, the first and second grooves 92, 94 may extend substantially from and between first and second sides 100, 102 (FIG. 3) of the base 80. As will be explained in more detail below, in the assembled configuration the first and/or second grooves 92, 94 may be sized and shaped to mate or otherwise slidably engage with the first and second pins 70, 72. In this regard, in some configurations, the first and/or second grooves 92, 94 may include a substantially arcuate cross-sectional shape, or otherwise define a portion of a cylinder.

Figure 7B:
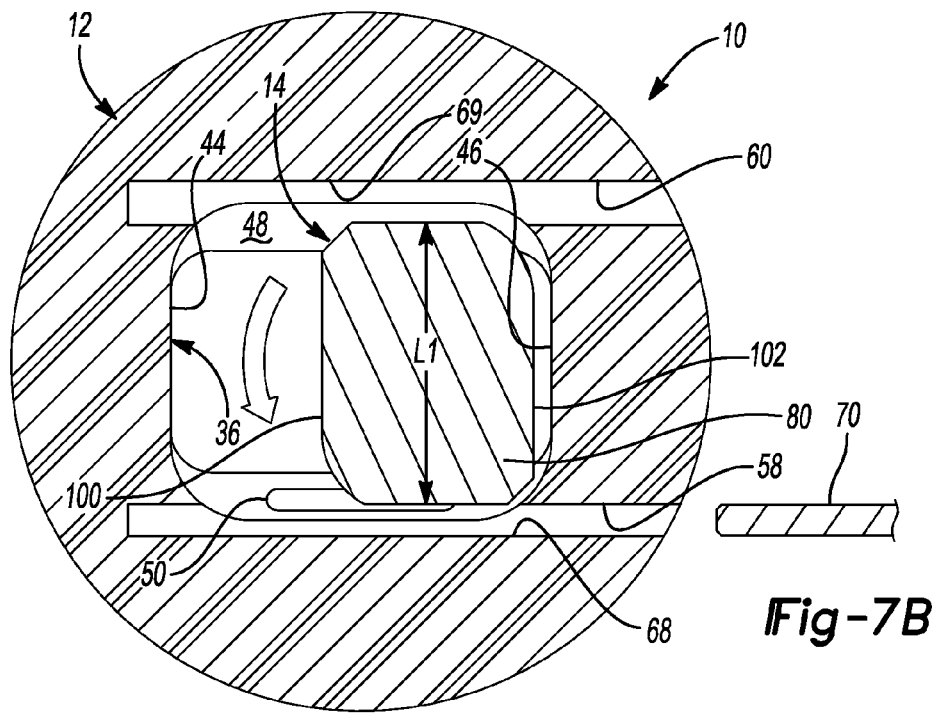
FIG. 7B is a cross-sectional view of the adjustable humeral tray similar to FIG. 7A and showing the adjustable humeral tray in a second partially assembled configuration.

With reference to FIGS. 7A and 7B, the base 80 may include a length L1 extending along the first and second sides 100, 102, and a width W1 extending from and between the first and second sides 100, 102. The length L1 may be greater than the width W1 and greater than the distance D2 extending between the first and second portions 42a, 42b of the lip 42, while the width W1 may be less than the distance D2. As will be explained in more detail below, the length L1, the width W1, and the distance D2 may help the surgeon or user to assemble, and thereafter secure, the coupler 14 to the tray 12.

With reference to FIGS. 3 and 4, the step 82 may extend from the distal side 88 of the base 80 along an axis 106, and may include a peripheral surface 108. A first portion 108a of the peripheral surface 108 and a second portion (not shown) of the peripheral surface may each be substantially coplanar with the first and second sides 100, 102 of the base 80. A third portion 108c and a fourth portion (not shown) of the peripheral surface 108 may be radially inwardly offset from the first and second sides 96, 98 of the base 80. The third portion 108c may be substantially parallel to the fourth portion and substantially perpendicular to the first portion 108a and the second portion. In this regard, the peripheral surface 108 may include first and second arcuate or radiused portions 108e, 108f extending from and between the first and third portions 108a, 108c and the second and fourth portions, respectively. As illustrated in FIG. 4, the first and second radiused portions 108e, 108f may define a maximum linearly-extending distance D3 therebetween. The distance D3 may intersect the axis 106 and be less than or substantially equal to the width W1 and/or the distance D2. In this regard, as will be explained in more detail below, the first and second radiused portions 108e, 108f may slidably engage the first and second portions 42a, 42b of the lip as the user rotates the coupler 14 about the axis 106 within the cavity 36.

The stem 84 may extend from the step 82 and/or the base 80 along the axis 106. As illustrated, in some configurations the stem 84 may include a substantially cylindrical construct. It will be appreciated, however, that the stem 84 may include other shapes within the scope of the present disclosure. In this regard, as illustrated in FIG. 5, the size and shape of the stem 84 may correspond to the size and shape of a female mating portion 112 formed in the stem 16. Specifically, the stem 84 may include a male Morse taper configured to engage a female Morse taper 112 formed in the stem 16.

Figure 7C:
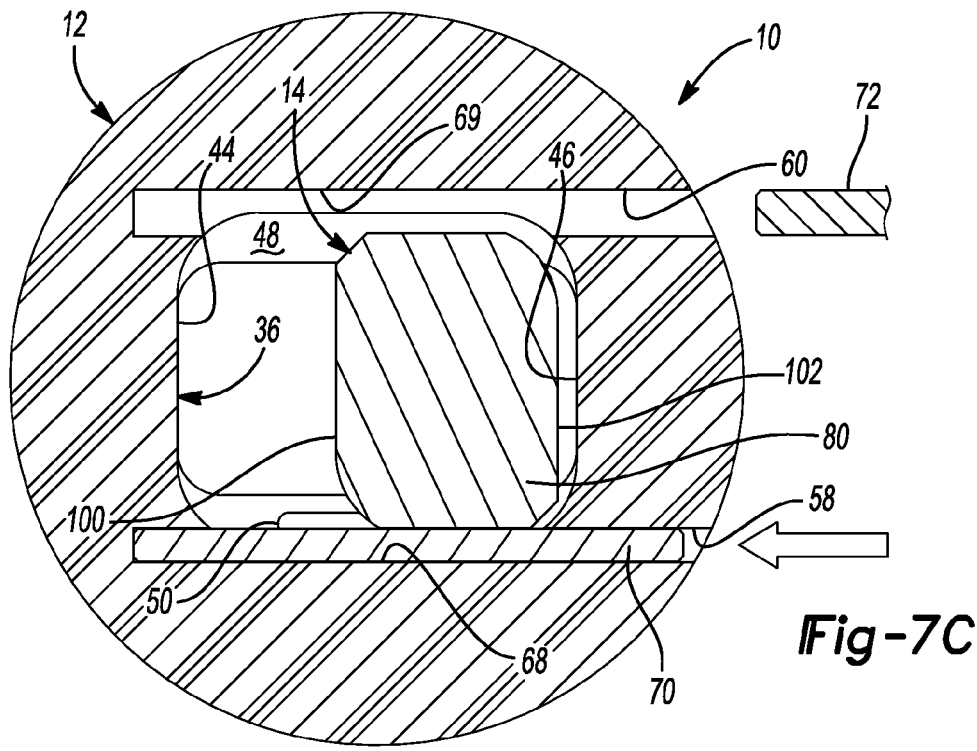
FIG. 7C is another cross-sectional view of the adjustable humeral tray similar to FIG. 7A and showing the adjustable humeral tray in a third partially assembled configuration.
Figure 7D:
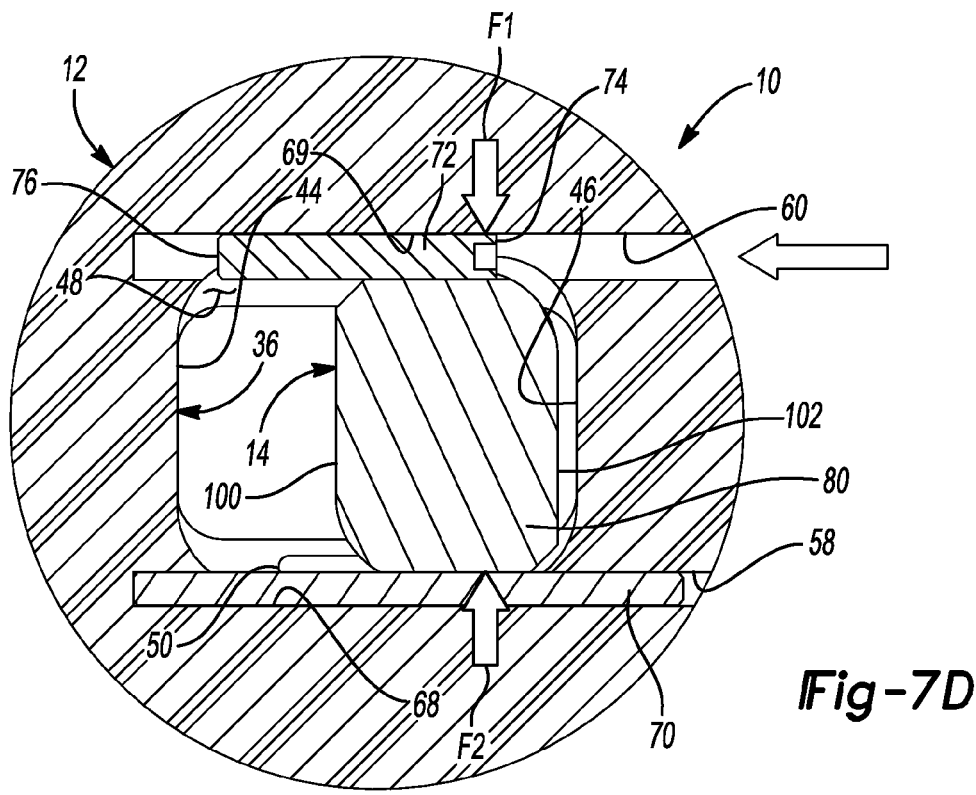
FIG. 7D is another cross-sectional view of the adjustable humeral tray similar to FIG. 7A and showing the adjustable humeral tray in a fully assembled configuration.
Figure 8:
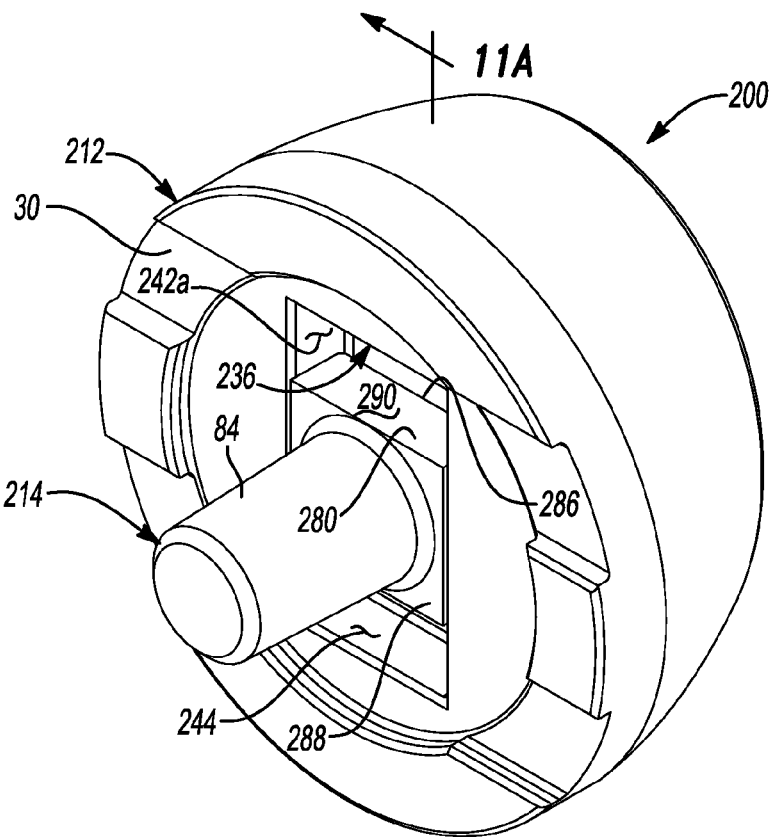
FIG. 8 is a perspective view of a first side of another adjustable humeral tray in accordance with the principles of the present disclosure.
Figure 9:
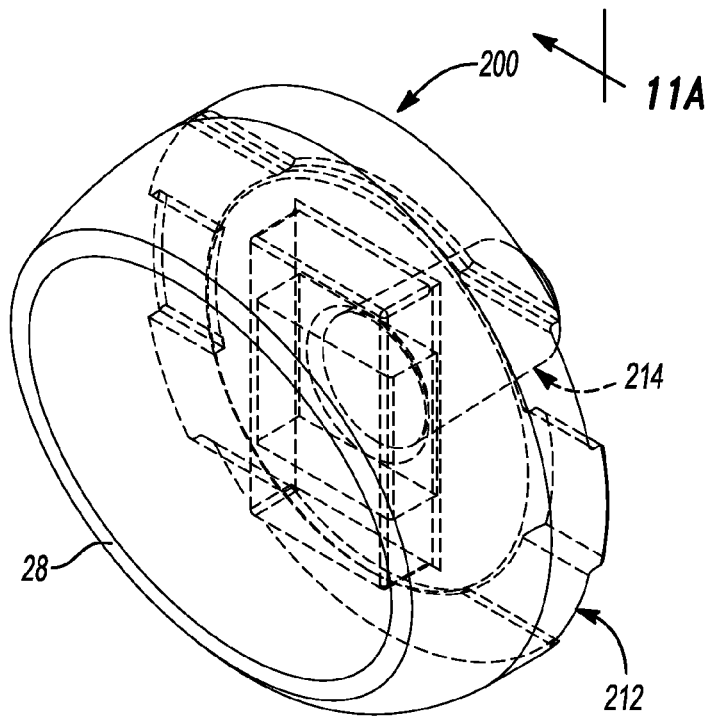
FIG. 9 is a perspective view of a second side of the adjustable humeral tray of FIG. 8.

With continued reference to FIGS. 1-7D, a method of assembling and using the adjustable implant 10 will now be described. With reference to FIG. 7A, the user may place the coupler 14 within the cavity 36 of the tray 12 such that the first and second sides 96, 98 of the base 80 are substantially aligned with, or otherwise facing, the first and second stop surfaces 44, 46 of the cavity 36. With reference to FIG. 7B, the user may rotate the coupler 14 about the axis 106 within the cavity 36 such that the first and second sides 96, 98 are substantially aligned with, or otherwise facing, the first and second channels 68, 69, respectively. As illustrated in FIG. 7C, the user may insert the first pin 70 into the first aperture 58 such that the first pin 70 is disposed within the first channel 68 and within the first groove 92. It will be appreciated that the first groove 92 of the coupler 14 may slidably engage the first pin 70. In this regard, the user may slide or otherwise move the coupler 14 to a desired position within the cavity 36. Specifically, as illustrated in FIG. 5, the user may move the coupler 14 into a position that minimizes an overhang 114 of the tray 12 relative to a resected or cut surface 116 of a humerus 118 or other bone when the stem 84 is coupled to the stem 16. As indicated above, the user may utilize the window 50 and/or the metering portion 52 to help with properly positioning the coupler 14 within the cavity 36. It will be appreciated that muscles, tendons, or other soft tissues (not shown) may be coupled to, or otherwise supported by, the tray 12. For example, soft tissues may be coupled to, or otherwise supported by, the glenosphere 20, which can mate with the glenosphere-receiving side 28 of the tray 12. Accordingly, as the surgeon adjusts the position of the tray 12 relative to the resected surface 116 of the humerus 118, the tray 12 can in turn adjust the position of the glenosphere 20, and the soft tissues supported by the glenosphere, and thus help the surgeon to pull or otherwise provide tension to the soft tissues.

As illustrated in FIG. 7D, the second pin 72 may be inserted into the second aperture 60 such that the second pin 72 is disposed within the second channel 69 and within the second groove 94. It will be appreciated that the second groove 94 of the coupler 14 may slidably engage the second pin 72. Once the user has established the desired position of the coupler 14 within the cavity 36, the user may further insert the second pin 72 within the second aperture 60 such that the taper of the second pin 72 causes the second pin 72 to apply a first force F1 on the coupler 14, and thereby causes the first pin 70 to apply a second force F2 (opposite the first force F1) on the coupler. The first and second forces F1, F2, and the corresponding frictional forces generated between the coupler 14 and the first and second pins 70, 72, can lock or otherwise secure the coupler 14 in the desired position within the cavity 36.

The stem 16 may be inserted into the humerus 118, and the stem 84 of the coupler 14 may be inserted into the female mating portion 112 of the stem 16. In this regard, it will be appreciated that the position of the coupler 14 within the tray 12 may be changed after the coupler 14 is secured to the stem 16 by inserting the second pin 72, in the manner described above, after coupler 14 is secured to the stem 16. The glenosphere 20 may be coupled to the glenosphere-receiving side 28 of the tray 12 and mated to the retainer 18 in a manner otherwise known in the art. Similarly, the retainer 18 may be coupled to the baseplate 22, and the baseplate 22 may be coupled to a glenoid 120 in a manner otherwise known in the art.

With reference to FIGS. 8-11B, another adjustable implant 200 constructed in accordance with the present teachings is illustrated. The adjustable implant 200 may be substantially similar to the adjustable implant 10 apart from any exceptions described below and/or shown in the figures. Accordingly, like reference numerals may be used to describe similar features and components, and similar features and components will not be described again in detail.

The adjustable implant 200 may include a tray 212 and a coupler 214. The tray 212 may include a cavity 236 defined by, or otherwise including, the first guide surface 38 and a peripheral surface. The peripheral surface may include a second guide surface 242a and a third guide surface (not shown) opposed to the second guide surface 242a, and first and second opposed ends or stop surfaces 244, 246. The second guide surface 242a and the third guide surface may be angled or otherwise taper inwardly from the coupler-receiving side 30 to the glenosphere-receiving side 28. In this regard, the cavity 236 may define a female Morse taper.

The coupler 214 may include a base 280 and the stem 84. The base 280 may include a proximal side 286, a distal side 288, and a peripheral edge or surface 290 extending from and between the proximal and distal sides 286, 288. The peripheral surface 290 may be angled or otherwise taper inwardly from the distal side 288 to the proximal side 286. In this regard, the base 280 may define a male Morse taper sized and shaped to mate with the female Morse taper of the cavity 236.

With continued reference to FIGS. 8-11B, a method of assembling and using the adjustable implant 200 will now be described. With reference to FIG. 11A, the user may place the coupler 214 within the cavity 236 of the tray 212 such that the proximal side 286 of the base 280 and the first guide surface 38 of the tray 212 define a space or gap 292 therebetween, and such that the peripheral surface 290 of the coupler 214 engages the peripheral surface 240 of the cavity 236. The gap 292 may have a height H, such that the peripheral surface 290 of the coupler 214 can slide or otherwise move along the second guide surface 242a and the third guide surface of the cavity 236. In this regard, the user may move the coupler 214 into a desired position with the cavity 236 in the manner described above with respect to the adjustable implant 10.

With reference to FIG. 11B, once the user has established the desired position of the coupler 214 within the cavity 236, the user may apply a force F on the coupler 214 in a direction substantially parallel to the axis 106. The force F may reduce the height H of the gap 292 and thereby cause the peripheral surface 240 to apply opposed forces on the peripheral surface 290 of the coupler 214. The opposed forces on the peripheral surface 290 of the coupler 214 and the corresponding frictional forces generated between the coupler 214 and the peripheral surface 290, can lock or otherwise secure the coupler 214 in the desired position within the cavity 236. In this regard, it will be appreciated that the coupler 214 may be secured within the cavity 236 using a press-fit configuration.

It will be appreciated that the adjustability of the implants 10, 200 relative to the humerus 118 can allow the surgeon to minimize or otherwise eliminate the overhang 114 of the implant 10, 200, including the tray 12, 212, relative to the resected surface 116 of the humerus 118, by selecting and adjusting the position of the implant 10, 200 relative to the resected surface 116 (e.g., centering the implant 10, 200 relative to the resected surface 116). Moreover, it will be appreciated that the adjustability of the implants 10, 200 relative to the humerus 118 can allow the surgeon to provide tension to certain soft tissues such as muscles and tendons, for example.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

What is claimed is:

1. An adjustable humeral implant comprising:
   a humeral tray having a humeral coupler receiving portion and first and second apertures in communication with the humeral coupler receiving portion;
   a humeral coupler having a humeral tray mating portion and a stem portion extending from the humeral tray mating portion along a first axis, the humeral tray mating portion translatable within the humeral coupler receiving portion in a direction transverse to the first axis;
   an adjustment member slidably received by an inferior edge of the humeral tray mating portion and within the first aperture; and
   a lock member slidably received by a superior edge of the humeral tray mating portion and within the second aperture.

2. The adjustable humeral implant of claim 1, wherein the humeral coupler receiving portion defines a channel, and wherein the humeral tray mating portion is operable to translate within the channel.

3. The adjustable humeral implant of claim 1, wherein the humeral tray mating portion translates within the humeral coupler receiving portion in a direction substantially perpendicular to the first axis.

4. The adjustable humeral implant of claim 1, wherein the first and second apertures include first and second openings, respectively, in an exterior peripheral surface of the humeral tray.

5. The adjustable humeral implant of claim 1, wherein the humeral coupler is rotatably received within the humeral coupler receiving portion.

6. The adjustable humeral implant of claim 5, wherein the humeral coupler is rotatable within the humeral coupler receiving portion about the first axis and translatable within the humeral coupler receiving portion in a direction substantially perpendicular to the first axis.

7. The adjustable humeral implant of claim 1, wherein the humeral tray mating portion is press-fit within the humeral coupler receiving portion.

8. The adjustable humeral implant of claim 1, wherein the stem portion includes a male taper and the humeral coupler receiving portion includes a female taper, and wherein the male taper is configured to frictionally engage the female taper.

9. An adjustable humeral implant comprising:
   a humeral coupler having a base and a stem extending from the base along a longitudinal axis; and
   a humeral tray having a glenosphere-facing side and an opposed humerus-facing side, the humerus-facing side including a recess at least partially defined by a bottom surface and opposed flanges, the recess configured to slidably receive the base of the humeral coupler such that the opposed flanges secure the base within the recess,
   wherein the base is translatable within the recess in a direction substantially perpendicular to the longitudinal axis,
   wherein the humeral coupler is rotatably received by the recess for rotation about the longitudinal axis.

10. The adjustable humeral implant of claim 9, further comprising an adjustment member and a lock member, the adjustment member slidably received by an inferior edge of the humeral coupler, the lock member slidably received by a superior edge of the humeral coupler.

11. The adjustable humeral implant of claim 10, wherein the humeral tray includes first and second apertures in communication with the recess and configured to receive the adjustment member and the lock member, respectively.

12. The adjustable humeral implant of claim 11, wherein the first and second apertures include first and second openings, respectively, in an exterior peripheral surface of the humeral tray.

13. A method of assembling an adjustable humeral implant including a humeral tray and a humeral coupler configured to translate relative to the humeral tray, the method including:
   inserting a stem into a humerus having a cut surface, the stem extending from a base of the humeral coupler along a longitudinal axis, the base translatable within a recess of the humeral tray in a direction substantially perpendicular to the longitudinal axis;
   rotating the humeral coupler about the longitudinal axis of the stem;
   translating the humeral tray relative to the humeral coupler in a direction substantially parallel to the cut surface from a first position to a second position; and
   securing the humeral tray in the second position.

14. The method of claim 13, wherein securing the humeral tray in the second position includes:
   inserting an adjustment member and a lock member into the humeral tray, the adjustment member slidably received by an inferior edge of the humeral coupler, and the lock member slidably received by a superior edge of the humeral coupler.

15. The method of claim 13, wherein securing the humeral tray in the second position includes press-fitting the humeral coupler to the humeral tray.

16. The method of claim 13, further comprising:
 determining a first overhang distance of the humeral tray relative to the cut surface in the first position; and
 determining a second overhang distance of the humeral tray relative to the cut surface in the second position, wherein the second overhang distance is less than the first overhang distance.

\* \* \* \* \*